United States Patent [19]

Mabille et al.

[11] 3,962,363

[45] June 8, 1976

[54] PROCESS FOR SELECTIVELY PRODUCING PARAXYLENE

[75] Inventors: Albert Mabille, Saint-Servais; Inaki de Aguirre, Heverlee, both of Belgium; Christian Marcilly, Montesson, France

[73] Assignee: Institut Francais du Petrole des Carburants et Lubrifiants, Rueil-Malmaison, France

[22] Filed: Sept. 25, 1974

[21] Appl. No.: 509,147

[30] Foreign Application Priority Data

Sept. 27, 1973 France .............................. 73.34746

[52] U.S. Cl. ...................... 260/671 M; 260/671 R; 260/672 T
[51] Int. Cl.² ....................... C07C 3/52; C07C 3/62
[58] Field of Search ........ 260/672 T, 671 R, 671 A, 260/671 M

[56] References Cited

UNITED STATES PATENTS

| 2,954,414 | 9/1960 | Hoff et al. | 260/672 |
|---|---|---|---|
| 3,031,513 | 4/1962 | Earhart et al. | 260/671 |
| 3,350,469 | 10/1967 | Ryan | 260/672 |
| 3,551,510 | 12/1970 | Pollitzer et al. | 260/672 |
| 3,751,506 | 8/1973 | Burress | 260/671 |
| 3,775,511 | 11/1973 | Shue | 260/671 |

*Primary Examiner*—Delbert E. Gantz
*Assistant Examiner*—C. E. Spresser
*Attorney, Agent, or Firm*—Millen, Raptes & White

[57] ABSTRACT

Process for selectively producing paraxylene comprising reacting toluene with methanol, dimethylether or vinyl chloride and at least one polymethylbenzene having 4 to 6 methyl groups or a condensed polymethylaromatic compound or a complex containing the same, in the presence, as catalyst, of a zeolite whose pore diameter is at least 7.5 A.

14 Claims, No Drawings

PROCESS FOR SELECTIVELY PRODUCING PARAXYLENE

This invention concerns a new process for selectively producing paraxylene.

Paraxylene is known as the most used of the three xylene isomers. In particular, it is converted to terephthalic acid or to dimethylterephthalate which has numerous applications for the manufacture of resins, fibers (tergal for example), polyester films and plastics.

Paraxylene can be obtained by conversion of various aromatic hydrocarbons, more particularly toluene, metaxylene and trimethylbenzenes. The most known of these operations are:
1. alkylation of toluene by methanol,
2. transalkylation of toluene by trimethylbenzenes,
3. isomerization of metaxylene.

The alkylation of toluene by methanol is the only reaction from the 3 above-mentioned ones whereby paraxylene can be obtained with a sufficient selectivity.

This reaction was therefore of high interest since toluene is an unexpensive reactant which has only a few petrochemical applications and the methanol price will probably be obtained in the future at a much lower price than now.

It has now been discovered that the selectivity to paraxylene may be increased by reacting together toluene, at least one polymethylbenzene and a reactant selected from methanol, dimethylether and methylchloride.

This invention concerns a new process for selectively producing paraxylene by reaction or combination of reactions using as reactants toluene, one or more polymethylbenzenes and another reactant selected from methanol, dimethylether and methyl chloride.

By the present invention, it is possible to obtain paraxylene with selectivities higher than those obtained according to the prior art and which can be as high as 60–70% of paraxylene in the xylenes. The invention thus results in an increased yield in the one or more steps of separating paraxylene and in a corresponding decrease of the capacity of the isomerization unit optionally used for completing the xylene conversion.

As polymethylbenzenes we can use, for example, tetramethylbenzenes, pentamethylbenzenes, hexamethylbenzenes, condensed polymethyl aromatic compounds or complex molecules, a portion of which consists of a methylbenzene, a polymethylbenzene or a condensed polymethyl aromatic compound.

When using simple polymethylbenzenes, i.e those containing a single aromatic ring, it is convenient to select among the polymethylbenzenes those containing at least four methyl groups fixed on the nucleus: thus we can make use of tetramethylbenzenes, pentamethylbenzenes and hexamethylbenzenes but the use of trimethylbenzenes will be avoided. As a matter of fact, the trans- alkylation of toluene by trimethylbenzenes does not provide for a selectivity to paraxylene higher than about 35%, due to the fact that in the mixtures of trimethylbenzenes, a predominent proportion of 1,2,4 trimethylbenzene is to be found: the release of a methyl group of said 1,2,4 trimethylbenzene (this methyl group being transferred on the toluene to form essentially paraxylene) occurs preferentially in position 1, leading to metaxylene and lowering accordingly the selectivity of the paraxylene production. On the contrary, when the transalkylation of toluene is carried out by means of a $C_{10}^+$ polymethylbenzene (for example tetramethylbenzene) the selectivity of the paraxylene production is higher than 50%.

In such a case where $C_{10}^+$ polymethylbenzenes (tetra, penta and hexamethylbenzenes) are used since these products are not available in a large amount on the market of the aromatic compounds, it is possible, in a first step, to manufacture them by the reacting trimethylbenzenes or xylenes or even toluene with the selected reactant (methanol, dimethylether or methyl chloride). Thus, when using as $C_{10}^+$ polymethylbenzenes, the tetra, penta or hexamethylbenzenes, the process of the invention can be conducted:

either in a single step by simultaneously reacting toluene, the one or more $C_{10}^+$ polymethylbenzenes and the selected reactant (methanol, dimethylether or vinyl chloride), or in two steps, the first step of which provides for the manufacture of the one or more $C_{10}^+$ polymethylbenzenes by alkylation, by means of methanol, dimethylether or vinyl chloride, or partially demethylated polymethylbenzenes (for example by alkylation of trimethylbenzenes when it is desired to manufacture tetramethylbenzenes), the second of said steps being destined to the production of xylenes by action of toluene on the $C_{10}^+$ polymethylbenzenes prepared in the first step.

The present invention may thus comprise one or two steps:

1. in the single step process, a charge containing toluene, said reactant (methanol for example) and polymethylbenzenes having 4 or more methyl groups, is reacted at a temperature within a narrow range depending on the catalyst activity so as to reduce the occurrence of parasitic reactions which might be detrimental to the selectivity. The object of the operation is to favour the two following reactions:

a. transalkylation of toluene by means of tetramethylbenzenes or higher polymethylbenzenes giving xylenes and trimethylbenzenes and/or higher polymethylbenzenes;

b. alkylation of trimethylbenzenes or more generally of $C_9^+$ polymethylbenzenes, by means of said reactant (methanol for example) to tetramethylbenzenes and/or higher polymethylbenzenes which will be again reacted with toluene. The process can be conducted at will in the presence or the absence of a gaseous diluent such as hydrogen or an inert gas (nitrogen, argon, etc . . . ). It is preferred, according to this invention, to proceed in the presence of hydrogen, provided that no use is made of a catalyst containing a highly hydrogenating agent which would lead to a substantial hydrogenation of the aromatic compounds followed by a decyclization of naphthenes and cracking of the paraffins.

In this single step process, it is convenient to proceed in unique vapor phase.

The operating conditions of the single step process of the invention are as follows:

the molar composition of the charge is within the following range:
   20 to 95% of toluene and,
   2 to 60% of said reactant (e.g methanol),
   2 to 60% of $C_{10}^+$ polymethylbenzenes and, preferably:
   40 to 85% of toluene and,
   5 to 40% of said reactant or $C_{10}^+$ polymethylbenzenes, the temperature is in the range from 50° to 450°C and preferably, from 150° to 350°C, the pressures are from 1 bar (atmospheric pressure) to 150 bars and, preferably, from 1 to 60 bars, the feeding spatial velocity, expressed in volume of charge per volume of catalyst and per hour, is from 0.05 to 10 and, preferably, from 0.1 to 5, when operating in the presence of hydrogen, the molar ratio of $H_2$ to the feed charge is from 0.1 to 20 and, preferably, from 1 to 8.

The selection of the operating conditions must always take into account the requirement of a vapor phase operation.

The single step embodiment of the process of the invention provides for xylene contents of the organic phase of the effluents as high as about 60% with paraxylene proportions from 45 to 70% in the mixture of the three xylenes and from 50 to 80% in the mixture of para- and meta-xylenes.

2. In the two step process, we proceed separately to an alkylation step by means of the said reactant (e.g methanol), of compounds of the type of polymethylbenzenes, acceptors of $CH_3$ groups, partially dimethylated and in another step, to the transalkylation of toluene by means of the product obtained in the first step. Thus the $CH_3$ group acceptors used as reactants may be, for example, the trimethylbenzenes which lead, at the end of the first step, to the production of tetramethylbenzenes.

As in the case of a single step process, the two step process may also be conducted at will in the presence of hydrogen and/or an inert gas provided that, in the presence of hydrogen, the use of a catalyst containing a highly hydrogenating agent is prohibited.

The alkylation step of the first step must be conducted in the vapor phase but, on the contrary, the step of the toluene transalkylation by means of $C_{10}^+$ polymethylbenzenes may be conducted as well in the vapor phase as in the liquid or optionally mixed phase.

Apart from the composition of the feed charges, the above-described operating conditions can be used for each of the steps of this two step embodiment.

The molar composition of the feed charge in the first step is within the following range:

10 to 95% of trimethylbenzenes,
5 to 90 % of said reactant (e.g methanol and preferably, 30 to 80% of trimethylbenzenes and,
20 to 70% of said reactant.

The molar composition of the feed charge for the reaction of toluene transalkylation by means of $C_{10}^+$ polymethylbenzenes is within the range of:

40 to 98 % of toluene, and
2 to 60 % of polymethylbenzes and, preferably from 50 to 90 % of toluene and,
10 to 50 % of polymethylbenzenes.

This two step embodiment of the present invention provides for xylene contents and xylene selectivities comparable with those obtained in the single step embodiment.

All the acid catalysts might optionally be used in the one or more steps of the process according to the invention. The preferred catalysts are those which favour the alkylation reactions as compared to the isomerization reactions of aromatics. As non-limitative examples of such catalysts we can mention the amorphous silica-aluminas, zeolites, silica-magnesiae, silica-zirconia, boron-oxide-aluminas, magnesia-aluminas etc . . . The Friedel-Craft catalysts ($AlCl_3$, supported $AlCl_3$ for example) may also be used, but most of them have the inconvenience of having a too high isomerization effect.

Accordingly, among the preceding catalysts, we will use the zeolites having minimum pore diameters of 7,5 to 8 A (i.e a sufficiently large diameter for giving passage at least to the molecules of trimethylbenzenes: among the molecular sieves which are convenient we can mention in a non-restrictive manner: offretite, mordenite with large pores, zeolite $\Omega$, X sieves and particularly, Y sieves.

Most of these sieves originally contain very substantially alkaline metal cations (particularly sodium). Accordingly, they have no catalytic activity or only a very small one. It is therefore necessary to remove said cations and replace them by others which give to the zeolite a good activity. These sieves are thus exchanged in such a manner as to remove 50% and, preferably, 80% at least of the alkaline metal cations. The replacement may be carried out by means of ammonium ions decomposable by heat to gaseous ammonia which thus escape from the zeolite structure and to $H^+$ protons which are kept inside the structure as compensation cations. It is also possible to introduce plurivalent metal cations into the structure by exchange of the original alkaline ions or preceding ammonium ions: in the case of Y sieves, for example, we can introduce by this way alkaline earth metals or rare earths.

In some cases, for example that of offretite, the original cations may be alkyl ammonium cations which are also thermally decomposable; it is then no longer necessary to exchange cations for obtaining a good catalytic activity.

The following examples are given for illustrating the invention but are not intended to be condidered as limiting the scope thereof.

EXAMPLE 1

1,000 g of a commercial hydrated Y-Na sieve, containing about 8% by weight of sodium (sold on the trade by Union carbide company under the trade mark SK 40) having a ratio of a $SiO_2/Al_2O_3$ close to 5, is suspended in an ammonium nitrate aqueous solution at a 3M concentration; the volume of the solution corresponding to an amount of ammonium ions equal to 10 times the amount of sodium ions present in the introduced mass of zeolite. The solution is brought to 90°C for 6 hours, filtered and subjected to a second identical exchange. The solid is filtered and washed, then suspended into 5 liters of an aqueous solution containing 1 650 g of $Ce(NO_3)_3$, 6 $H_2O$ and 306 g of $NH_4NO_3$. The temperature is maintained at 90°C for 4 hours. The solid is filtered and repeatedly washed with distilled water. The zeolite is then roasted at 500°C for 2 hours in an air stream, and then shaped as pills.

Its analyzis indicates a Na content of 1.8% by weight and a cerium content of 9.3% by weight.

EXAMPLE 2 (comparative example)

The preceding product, in the form of pills, is tested as catalyst for alkylation of toluene by means of methanol in the following conditions:

Molar composition of the feed charge: toluene 60% methanol 40%
Hydrogen at atmospheric pressure
Feeding spatial velocity pph × ⅓ (g of feed charge per g of catalyst and per hour), molar ratio $H_2$/feed charge = 3

The following table I gives the results obtained at different temperatures of reaction.

The results given in Table II are obtained at 260°C and with a pph = ⅔, the other operating conditions being unchanged.

TABLE I

| Temp. °C | %Tol. | %Xyl. | %TMB | %P. Xyl / Σ Xyl | %M. Xyl / Σ Xyl | % P. Xyl / P.Xyl+M.Xyl |
|---|---|---|---|---|---|---|
| 240 | 95.4 | 3.8 | 0.8 | 55.0 | 25.0 | 68.8 |
| 250 | 89.4 | 9.1 | 1.5 | 51.8 | 26.0 | 66.6 |
| 260 | 84.1 | 13.1 | 2.8 | 48.1 | 26.1 | 64.8 |
| 280 | 77.7 | 19.3 | 3.0 | 48.0 | 32.7 | 59.5 |

Tol. = Toluene
Xyl. = Xylenes
TMB = Trimethylbenzene(s)

TABLE II

At 260° C and pph = ⅔, the following results have been obtained:

| TEMP. °C | %Tol. | %Xyl. | %TMB | %P.Xyl / Σ Xyl | %M.Xyl / Σ Xyl | % P.Xyl / P.Xyl+M.Xyl |
|---|---|---|---|---|---|---|
| 260 | 92.8 | 5.7 | 1.5 | 54.0 | 25.0 | 68.4 |

EXAMPLE 3

This is an example of the two step process for selectively manufacturing paraxylene, according to the invention.

In a first step, the catalyst of example 1 is used as catalyst for alkylation of 1,2,4 trimethyl benzene by means of methanol in the following conditions:

Molar composition of the feed charge: 60% of 1,2,4 trimethylbenzene and 40% of methanol,
Atmospheric hydrogen pressure
Feeding spatial velocity: pph = ⅓
Molar ratio of $H_2$/feed charge: 3

TABLE III

In this table, the results obtained at different temperatures are reported.

| TEMPE °C | %Xyl. | %TMB | % T₄MB | %P₅MB | %1,2,4 TMB / Σ TMB | 1,2,4,5 T₄MB / Σ T₄MB |
|---|---|---|---|---|---|---|
| 180 | 5.0 | 85.6 | 9.4 | — | 99.0 | 71.4 |
| 200 | 4.9 | 79.8 | 14.3 | 1.0 | 98.2 | 62.0 |
| 220 | 15.0 | 51.3 | 31.8 | 1.9 | 91.5 | 55.6 |
| 230 | 16.2 | 44.9 | 36.8 | 2.1 | 88.5 | 51.0 |

T₄MB = tetramethylbenzene(s)
P₅MB = pentamethylbenzene(s).

It may be observed that the reactivity of 1,2,4 trimethylbenzene is substantially higher than that of toluene in the reaction of alkylation with methanol.

The $C_{10}^+$ polymethylbenzenes obtained at 230°C are separated from the remaining portion of the effluents by distillation and admixed with toluene in the following proportions:

Toluene: 68 % molar, $C_{10}^+$ polymethylbenzenes: 32% molar.

In the second step, the solid of example 1 is used as catalyst for transalkylation of toluene by the $C_{10}^+$ polymethylbenzenes in the following conditions:
Hydrogen pressure: atmospheric
Feeding spatial velocity: pph = ⅓
Molar ratio $H_2$/ feed charge = 3

TABLE IV

This table reports the results obtained at different temperatures.

| Tem. °C | %Tol. | %Xyl. | % TMB | % T₄MB | % P₅MB | %P.Xyl / Σ Xyl | %P.Xyl / P.Xyl+M.Xyl |
|---|---|---|---|---|---|---|---|
| 240 | 61.3 | 5.2 | 7.9 | 25.2 | 0.4 | 59.0 | 72.3 |
| 260 | 54.0 | 10.3 | 14.8 | 20.2 | 0.7 | 56.9 | 65.4 |
| 280 | 48.5 | 16.3 | 20.4 | 13.8 | 1.0 | 54.0 | 60.8 |

It is apparent that the paraxylenes are obtained with selectivities higher than those achieved by alkylation of toluene with methanol.

EXAMPLE 4

This is an example of a single stage process for the selective production of paraxylene.

The catalyst of example 1 is tested with a charge consisting of a mixture of toluene with 1,2,4,5 tetramethylbenzene and methanol in the following conditions:

Molar composition of the feed charge: toluene 65 %, 1,2,4,5 T₄MB 12 %, methanol 23 %.
Hydrogen pressure: atmospheric.
Feeding spatial velocity: pph = ⅓
Ratio $H_2$/ feed charge = 3

TABLE V

This table reports the results obtained at different temperatures.

| Tem. °C | %Tol. | %Xyl. | % TMB | %T₄MB | %P.Xyl / Xyl | % P.Xyl / P.Xyl+M.Xyl |
|---|---|---|---|---|---|---|
| 240 | 67.6 | 14.8 | 10.3 | 7.3 | 64.3 | 73.7 |
| 260 | 63.0 | 18.7 | 11.9 | 6.4 | 59.8 | 64.1 |
| 280 | 54.5 | 21.6 | 16.9 | 7.0 | 55.2 | 59.9 |
| 310 | 41.9 | 31.3 | 21.6 | 5.2 | 49.6 | 54.1 |

It is observed that this process provides for very high selectivities of paraxylene which are even given higher in this case than those obtained by the two step process.

EXAMPLE 5 (comparative)

This is an example of a single step process similar to that of example 4, except that 1,2,4 trimethylbenzene is used in lieu of 1,2,4,5 tetramethylbenzene.

The catalyst of example 1 is tested with a charge consisting of a mixture of toluene, 1,2,4 trimethylbenzene and methanol in the following conditions:

Molar composition of the feed charge: toluene 65 %, 1,2,4 TMB 12%, methanol 23%.
Hydrogen pressure: atmospheric
Feeding spatial velocity: pph = ⅓
Ratio $H_2$/feed charge = 3

TABLE VI

This table reports the results obtained at different temperatures.

| Tem. °C | %Tol. | %Xyl. | % TMB | % T₄MB | % P.Xyl / Xyl | %P.Xyl / P.Xyl+M.Xyl |
|---|---|---|---|---|---|---|
| 240 | 71.3 | 18.4 | 6.2 | 4.1 | 35.2 | 41.7 |
| 260 | 66.2 | 24.3 | 5.1 | 4.4 | 32.9 | 38.1 |

It is apparent that the use of 1,2,4 TMB does not provide so high selectivity of paraxylene as those obtained with 1,2,4,5 T₄MB.

EXAMPLE 6

This is a second example of a single step process for the selective production of paraxylene.

The catalyst of example 1 is tested with a charge consisting of a mixture of toluene, tetramethylbenzenes (corresponding composition at the equilibrium, at 230°C: 1,2,3,4 T₄ MB: 14 %, 1,2,3,5 T₄MB: 50.6 %, 1,2,4,5 T₄MB: 35.4 %) and methanol in the following conditions:

Molar composition of the feed charge: toluene:54 %, tetramethylbenzenes:23%, methanol: 23 %.
Hydrogen pressure: atmospheric.
Feeding spatial velocity: pph = ⅓
Molar ratio H₂/feed charge = 3

TABLE VII

This table reports the results obtained at different temperatures.

| Tem. °C | %Tol. | %Xyl. | %TMB | % T₄MB | % P₅MB | %P.Xyl / Xyl | % P.Xyl / P.Xyl+M.Xyl |
|---|---|---|---|---|---|---|---|
| 260 | 47.1 | 16.9 | 12.9 | 22.2 | 0.9 | 56.9 | 61.3 |
| 280 | 42.6 | 20.4 | 17.3 | 18.4 | 1.3 | 53.0 | 56.6 |
| 310 | 35.2 | 29.5 | 23.5 | 10.0 | 1.8 | 45.8 | 50.6 |

We claim:

1. A process for producing xylenes of high paraxylene content, comprising reacting, in the vapor phase, a charge containing: (a) toluene, (b) methanol, and, (c) at least one polymethylbenzene containing at least 10 carbon atoms ($C_{10}^+$) and comprising at least 4 methyl groups fixed on the benzene ring, and the polymethylbenzene is tetramethylbenzenes, pentamethylbenzenes, hexamethylbenzenes or mixtures thereof, the molar composition of the said charge being 20 to 95 % of toluene, 2 to 60 % of methanol and 2 to 60 % of $C_{10}^+$ polymethylbenzenes, in the presence of an acid catalyst selected from the zeolites having pore diameters of at least 7.5 A.

2. A process according to claim 1 wherein the molar composition of the said charge is 40 to 85 % of toluene, 5 to 40 % of methanol and 5 to 40 % of $C_{10}^+$ polymethylbenzenes.

3. A process according to claim 1, wherein the temperature is from 150° to 500° C. and the pressure from 1 to 200 bars and the space velocity is from 0.05 to 10 weight of feed charge per weight of catalyst per hour.

4. A process according to claim 1, conducted in the presence of hydrogen, with hydrogen flow rates corresponding to molar ratios of H₂ to the feed charge in the range from 0.1 to 20.

5. A process according to claim 4 wherein the hydrogen is diluted with an inert gas.

6. A process according to claim 1 in which the acid catalyst is selected from offretite, zeolite Ω, mordenite, zeolite, of the faujasite structure, and synthetic molecular sieves of the X and Y type.

7. A process according to claim 6, in which the catalyst, before use, has been treated in order to obtain a metal-exchanged zeolite.

8. A process for producing xylenes of high paraxylene content, comprising a first step of reacting in the vapor phase, a charge containing (a) methanol and (b) at least one trimethylbenzene, the molar composition of the said charge being 5 to 90 % of methanol and 10 to 95 % of trimethylbenzenes, in order to obtain at least one $C_{10}^+$ polymethylbenzene, wherein the polymethylbenzene is tetramethylbenzenes, pentamethylbenzenes and hexamethylbenzenes, or mixtures thereof, and a second step, of reacting, in the vapor phase, toluene with at least one $C_{10}^+$ polymethylbenzene compound obtained in the first step, the molar composition of the feed charge for the reaction of toluene with at least one polymethylbenzene being 40 to 98 % of toluene and 2 to 60 % of polymethylbenzenes, in the presence of an acid catalyst selected from the zeolites having pore diameters of at least 7.5 A.

9. A process according to claim 8, in which the acid catalyst is selected from offretite, zeolite Ω, mordenite, zeolites of the faujasite structure and synthetic molecular sieves of the X and Y types.

10. A process according to claim 9, in which the catalyst, before use, has been treated in order to obtain a metal-exchanged zeolite.

11. A process according to claim 8 wherein, in the first step, the molar composition of the said charge is 20 to 70 % of methanol and 30 to 80 % of trimethylbenzenes and in the second step, the molar composition of the said feed charge is 50 to 90 % of toluene and 10 to 50 % of polymethylbenzenes.

12. A process according to claim 8, conducted in the presence of hydrogen, with hydrogen flow rates corresponding to molar ratios of H₂ to the charge in the range from 0.1 to 20, in each of the two steps.

13. A process according to claim 8 wherein the hydrogen is diluted with an inert gas.

14. A process according to claim 8, wherein the temperature in each of the two steps is from 150° to 300° C., and the pressure 1 to 150 bars and each of the two steps is carried out at a space velocity of 0.05 to 10 weight of feed charge per weight of catalyst per hour.

* * * * *

UNITED STATES PATENT AND TRADEMARK OFFICE
CERTIFICATE OF CORRECTION

PATENT NO. : 3,962,363
DATED : June 8, 1976
INVENTOR(S) : MABILLE ET AL

It is certified that error appears in the above-identified patent and that said Letters Patent are hereby corrected as shown below:

[73] Assignee: show read --INSTITUT FRANCAIS DU PETROLE--.

Signed and Sealed this

Twenty-fifth Day of January 1977

[SEAL]

Attest:

RUTH C. MASON
Attesting Officer

C. MARSHALL DANN
Commissioner of Patents and Trademarks